US00PP08959P

United States Patent [19]

Brizard

[11] Patent Number: Plant 8,959

[45] Date of Patent: Oct. 25, 1994

[54] SPRAY CARNATION NAMED WHITE OPALE

[75] Inventor: Jean Brizard, Paris, France

[73] Assignee: Laboratorie de Physiologie Vegetale, Le Pradet, France

[21] Appl. No.: 971,505

[22] Filed: Nov. 4, 1992

[51] Int. Cl.[5] ..... A01H 5/00
[52] U.S. Cl. ..... Plt./70.3
[58] Field of Search ..... Plt. 70.3

*Primary Examiner*—James R. Feyrer
*Assistant Examiner*—Bruce Campell
*Attorney, Agent, or Firm*—Tilton, Fallon, Lungmus & Chestnut

[57] ABSTRACT

A new and distinctive spray carnation cultivar particularly distinguished by its very large size flowers being generally white color and slightly pale pink in color at the center of the petal with a greenish base, the flowers being carried on erect stems.

1 Drawing Sheet

BACKGROUND OF THE NEW PLANT

This spray carnation cultivar originated as a sport in my nursery at Le Pradet, France. The sport was selected from a field of carnation varieties maintained at my nursery. This sport was selected because of the unusual flower coloration on a plant having moderately abundant foliage, favorable growth characteristics and resistance to *Fusarium oxysporum*. This plant most resembles Opale. (U.S. Plant Pat. No. 8,185) Opale is a spray carnation. However, Opale is pale cyclamen pink in color and has round, large petals. White Opale is white in color, and slightly pale pink at the center of the petal. Also, White Opale has fan-shaped petals. Under my direction, propagation was done by means of cuttings. This plant has been asexually reproduced at our nursery in Le Pradet, France. The initial success of the propagation was continued through several successive generations which proved that the new variety retained all of the distinguished characteristics hold true from generation to generation and appear to be firmly fixed.

DESCRIPTION OF THE DRAWINGS

My new spray carnation cultivar is illustrated by the accompanying photographic drawing which, in full color, shows the form and coloration of the flowers as they appear. The colors shown are as nearly true to those herein specified as is reasonably possible to obtain by conventional photographic procedures.

DESCRIPTION OF THE NEW PLANT

The following is a detailed description of my new carnation plant as observed from plants grown under greenhouse conditions in Le Pradet, France with the stated flower colors being according to the R.H.S. Colour Chart of the Royal Horticultural Society of London, England.

THE PLANT

Origin: Sport.
Parentage:
*Parent.*—Opale, U.S. Plant Pat. No. 8,185. The parent plant is so identified in my business records of the present cultivar maintained at the office of the Le Pradet, France nursery. Opale is a spray carnation, pale cyclamen pink in color with a flower diameter of 6 cm., large round petals, and a stem of 60 cm.

Classification:
*Botanic.*—*Dianthus Caryophyllus* L.
*Commercial.*—Spray carnation.
Form: An erect bush having at least four stems emitted near the ground having a vigorous and upright growth habit.
Height: About 91.8 cm. (at 8 months).
Cane length: Less than 15 cm. owing to the pinching.
Branching character: Moderately branched.
Strength: Rigid.
Foliage:
*Quantity.*—Moderately abundant.
*Number of leaves.*—More than 120.
*Size and shape of leaf.*—The leaf is 13×0.8 cm. (at the 7th node) and spindle-shaped.
*Margin type.*—Spindle-shaped, very little pronounced leaf roll, no thorny stif hair on the leaf margins.
*Texture.*—Leathery.
*Color.*—Upper side — RHS 137A. Under side — RHS 137A.

THE BUD

Size:
*Shape.*—Long.
*Diameter.*—1.4 cm average.
*Length.*—2.7 cm average.
*Color of petals.*—When sepals first divide, the same as full bloom; when the petals begin to unfurl, same as the full bloom.
Rate of opening: 100%.
Sepals:
*Shape.*—Joined at lower part and sharp-pointed at extremity and hooded over bud.
*Number.*—5.
*Color.*—Inside: Pea green RHS 149D and 137D. Outside: Scheele's green RHS 137A and 144B.
*When flowers open.*—The sepals curl back.
*Striae.*—Longitudinal striae.
Calyx:
*Shape.*—Cylindrical.
*Size.*—Long.
*Aspect.*—Smooth.
*Splitting.*—No.
Peduncle:

*Length.*—68.4 cm (in average).
*Character.*—Upright.
*Color.*—137B RHS.

THE FLOWER

Blooming habit: Recurrent and profuse.
Size of bloom: Very large.
*Diameter.*—About 6.3 cm.
*Depth.*—About 5 cm.
Borne: In a cluster. Number of flowers per cluster (Average): 6.
Shape: High center when bloom first opens and dome shaped when it matures.
Petalage:
*Number of petals.*—43–57.
*Number of florets.*—Yes in average, about 6.
*Form.*—Fan-shaped.
*Texture.*—Leathery.
*Arrangement.*—Imbricated.
*Appearance.*—Satiny.
*Color.*—Outer petals — 155D and 36D at center with a greenish base; reverse side — Inside petal — 155D and 36D at center with a greenish base.
Petaloids:
*Number.*—1 to 4.
*Size.*—Smaller than petals.
*Color.*—Same as petals.
Discoloration after full bloom: A little.
Persistence: Yes. Because this creation concerns a perpetual flowering carnation cultivated for the production of cut flowers, no observation was made on the quantitative value for persistance.

Lasting quality: As cut flower, at least 10 days.
Disease resistant: Resistant to *Fusarium oxysporum.*
Fragrance: Perceptible.

REPRODUCTIVE ORGANS

Stamens:
*Number.*—1 to 2.
*Arrangement.*—Around the ovary.
Anthers:
*Size.*—Less than 0.4 cm.
*Color.*—Whitish.
Filaments:
*Length.*—1.3 cm.
*Color.*—Whitish.
Pistils:
*Number.*—3 to 5.
Styles:
*Length.*—3.3 cm.
*Color.*—Whitish.
Stigmas: Whitish.
Character of ovaries: Ribbed.

I claim:

1. A new and distinctive spray carnation plant, substantially as herein shown and described, characterized in particular by its recurrent profuse production of very large size flowers, the petals of which are in general of ivory color and are slightly pale pink at the center with a greenish base; the flowers being carried on an erect stem.

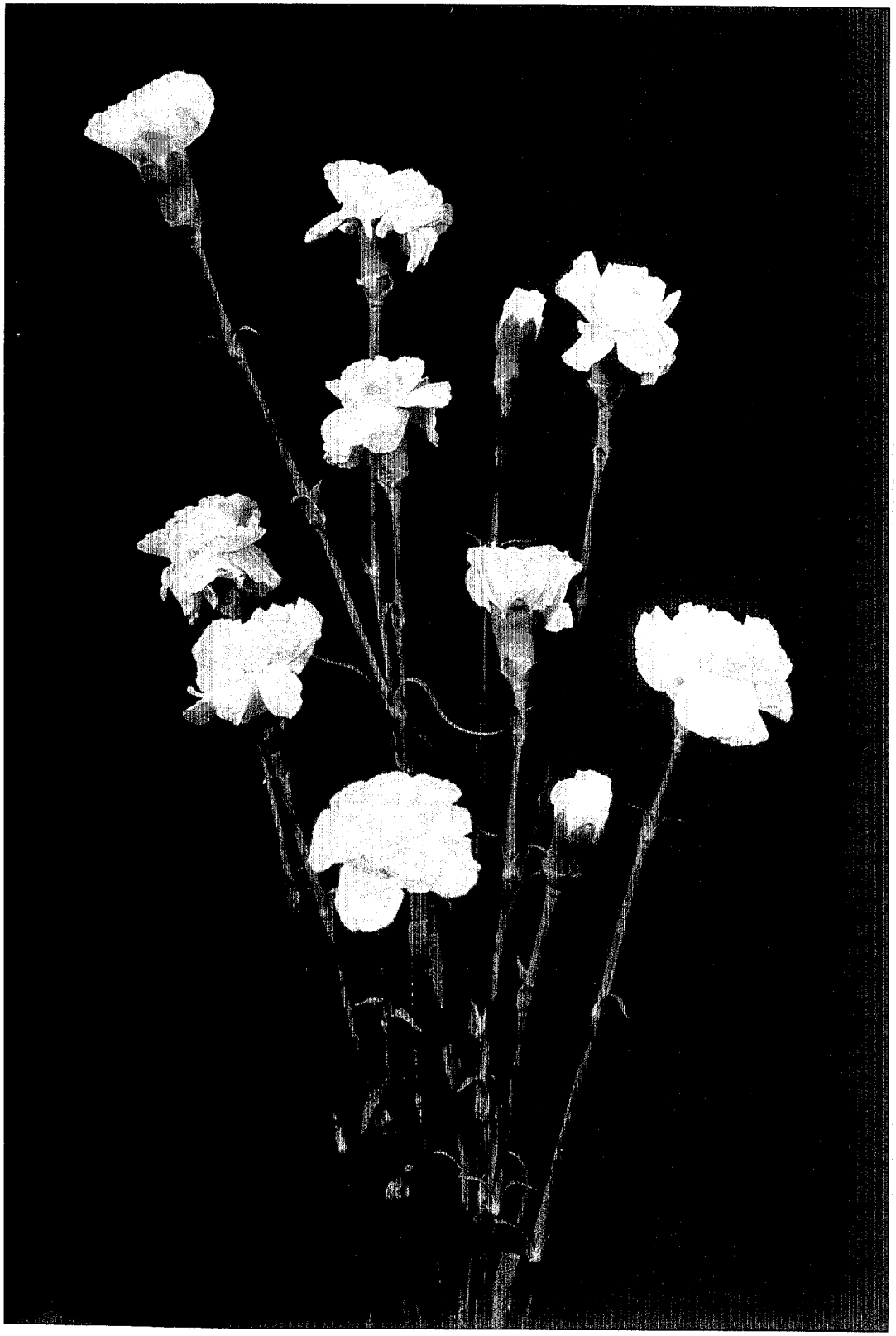

* * * * *